(12) United States Patent
Hershberger et al.

(10) Patent No.: US 7,494,509 B1
(45) Date of Patent: Feb. 24, 2009

(54) METHOD AND APPARATUS FOR PROVIDING A SHORT-STEMMED HIP PROSTHESIS

(75) Inventors: Troy W Hershberger, Warsaw, IN (US); Ryan C Lakin, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 472 days.

(21) Appl. No.: 10/892,460

(22) Filed: Jul. 15, 2004

Related U.S. Application Data

(63) Continuation-in-part of application No. 10/066,996, filed on Feb. 4, 2002, now abandoned.

(51) Int. Cl.
*A61F 2/36* (2006.01)
*A61F 2/32* (2006.01)

(52) U.S. Cl. ................. 623/23.35; 623/23.15; 623/22.4

(58) Field of Classification Search ... 623/23.11–23.41, 623/22.4–22.44, 22.11, 22.12, 20.35, 20.36; 606/84–89, 62, 67
See application file for complete search history.

(56) References Cited

U.S. PATENT DOCUMENTS

| | | | |
|---|---|---|---|
| 2,934,065 A | 4/1960 | Townley | |
| 3,064,645 A | 11/1962 | Ficat et al. | ..................... 123/23 |
| 3,893,196 A | 7/1975 | Hochman | |
| 3,965,490 A | 6/1976 | Murray et al. | |
| 4,004,300 A | 1/1977 | English | |
| 4,021,865 A | 5/1977 | Charnley | |
| 4,068,324 A | 1/1978 | Townley et al. | |
| 4,101,985 A | 7/1978 | Baumann et al. | |
| 4,141,088 A | 2/1979 | Treace et al. | |
| 4,279,042 A * | 7/1981 | Andriacchi et al. | ...... 623/23.15 |
| 4,283,799 A | 8/1981 | Pratt, Jr. et al. | |
| 4,310,931 A | 1/1982 | Muller | |
| 4,408,359 A | 10/1983 | Burstein et al. | |
| 4,516,277 A | 5/1985 | Butel | |
| 4,530,114 A | 7/1985 | Tepic | |
| 4,549,319 A * | 10/1985 | Meyer | ..................... 623/23.23 |
| 4,589,883 A | 5/1986 | Kenna | |
| 4,650,489 A | 3/1987 | Thompson | |
| 4,738,681 A | 4/1988 | Koeneman et al. | |
| 4,770,661 A | 9/1988 | Oh | |
| 4,792,339 A | 12/1988 | Tepic | |

(Continued)

FOREIGN PATENT DOCUMENTS

DE 39 034 38 A1 8/1990

OTHER PUBLICATIONS

"Why Suffer From Hip Pain?," Mar. 13, 2001, pp. 1-2, http://www.hippain.com/hip.html.

(Continued)

*Primary Examiner*—Alvin J Stewart
(74) *Attorney, Agent, or Firm*—Harness, Dickey & Pierce, P.L.C.

(57) ABSTRACT

A method of implanting at least a stem member of a femoral insert into an intramedullary canal of a femur. The method includes making an anterior incision for accessing the intramedullary canal, and inserting a stem member of the femoral insert into the intramedullary canal through the incision along an arcuate path defined by an arcuate profile of the stem member.

29 Claims, 14 Drawing Sheets

U.S. PATENT DOCUMENTS

| | | | |
|---|---|---|---|
| 4,795,471 A | 1/1989 | Oh | |
| 4,871,369 A | 10/1989 | Muller | |
| 4,895,573 A | 1/1990 | Koeneman et al. | |
| 4,988,359 A | 1/1991 | Frey et al. | |
| 5,007,931 A | 4/1991 | Smith | |
| 5,041,118 A | 8/1991 | Wasilewski | |
| 5,108,451 A | 4/1992 | Forte | |
| 5,258,035 A | 11/1993 | Hofmann et al. | |
| 5,314,489 A | 5/1994 | Hoffman et al. | |
| 5,458,651 A | 10/1995 | Lawes | |
| 5,507,829 A | 4/1996 | Thongpreda et al. | |
| 5,658,352 A | 8/1997 | Draenert | |
| 5,755,811 A | 5/1998 | Tanamal et al. | |
| 5,871,549 A | 2/1999 | Jayashankar et al. | |
| 5,888,210 A | 3/1999 | Draenert | |
| 6,120,544 A | 9/2000 | Grundei et al. | |
| 6,676,706 B1 * | 1/2004 | Mears et al. | 623/22.4 |
| 6,706,073 B2 * | 3/2004 | Draenert et al. | 623/22.46 |
| 6,860,903 B2 | 3/2005 | Mears et al. | |
| 6,953,480 B2 | 10/2005 | Mears et al. | |
| 6,991,656 B2 | 1/2006 | Mears | |
| 6,997,928 B1 * | 2/2006 | Penenberg | 606/81 |
| 7,004,972 B2 * | 2/2006 | Yoon | 623/22.4 |
| 2002/0099447 A1 | 7/2002 | Mears et al. | |
| 2002/0116067 A1 | 8/2002 | Mears et al. | |
| 2003/0065397 A1 * | 4/2003 | Hanssen et al. | 623/20.32 |
| 2003/0097135 A1 * | 5/2003 | Penenberg | 606/86 |
| 2003/0220698 A1 | 11/2003 | Mears et al. | |
| 2005/0171548 A1 * | 8/2005 | Kelman | 606/79 |

OTHER PUBLICATIONS

"How the Hip Works," Mar. 13, 2001, pp. 1-2, http://www.hippain.com/hipworks.html.

"Total Hip Replacement," Mar. 13, 2001, pp. 1-2, http://www.hippain.com/hip2.html.

"Total Hip Replacement Surgical Procedure," Mar. 13, 2001, pp. 1-5, http://www.hippain.com/hip3.html.

"Zimmer Ohio Orthopedics MAYO Hip System," Mar. 13, 2001, p. 1, http://www.zimmerohio.com/may2.html.

Article entitled "Less pain, quicker recovery, shorter hopsital stay for hip-replacement surgery" [undated].

Audette et al., Portable Television For Recording Emergency Treatment, Educational Television, pp. 21-25 (Oct. 1969).

Barrasso et al., Wirbelkörperexzision für die Behandlung von zervikalen Bandscheibenerkrankungen, Spondylosen und Rückenmarkstenosen (Vertebral body excision in the treatment of cervical disc disease, spondylosis and spinal stenosis), Orhopade, pp. 40-43, vol. 14 (1985) © Springer-Verlag (1985).

Barrasso, M.D. et al., Simplified Reaming of Deformed Femoral Canal in Total Hip Surgery, Orthopaedic Review, pp. 111-112, vol. XII, No. 9 (Sep. 1983).

Booth, Jr., M.D., Surgical Approaches to the Hip, Total Hip Arthroplasty, pp. 1-13 (1988).

Brochure, A practical approach to Minimally Invasive Hip Surgery, posterior approach, Microplasty™ minimally invasive hip program, Biomet Orthopedics, Inc., (Jun. 2003).

Brochure, Frequently Asked Questions, Microplasty™ managing arthritis, Biomet Rapid Recovery Program [undated].

Brochure, Frequently Asked Questions, Microplasty™ minimally invasive joint surgery, Biomet Rapid Recovery Program [undated].

Brochure, The only complete solution for rapid recovery™, Microplasty™ minimally invasive program (Oct. 2003).

Callaghan, M.D., Skeptical perspectives on minimally invasive total hip arthroplasty, Point of View, Bulletin, American Academy of Orthopaedic Surgeons, American Association of Orthopaedic Surgeons, vol. 51, No. 6, Dec. 2003.

Callahan, M.D. et al., Cervical Facet Fusion for Control of Instability following Laminectomy, The Journal of Bone and Joint Surgery, pp. 991-1002, vol. 59-A, No. 8 (Dec. 1977).

Dedushkin, M.D. et al., Orthopaedic Aspects of the Afghan War: The Soviet Experience, Techniques in Orthopaedics®, pp. 225-230, vol. 10, No. 3 (1995).

Fulkerson, M.D. et al., Anatomy and Osteotomy of the Greater Trochanter, Arch Surg, pp. 19-21, vol. 114, (Jan. 1979).

Hendrikson, M.D. et al., Anterior Approach to Resurfacing Arthroplasty of the Hip: A Preliminary Experience, pp. 131-135, vol. 47, No. 3, Connecticut Medicine, Mar. 1983.

Hoffinger, M.D. et al., Primary Ceramic Hip Replacement: A Prospective Study of 119 Hips, Orthopedics, vol. 14, No. 5 (May 1991).

Huo, M.D., et al., Cementless Total Hip Arthoplasties Using Ceramic-on-Ceramic Articulation in Young Patients, A Minimum 5-Year Follow-up Study, The Journal of Arthroplasty, pp. 673-678, vol. 11, No. 6, (1996).

Huo, M.D. et al., Effect of Preoperative Autologous Blood Donation and Intraoperative and Postoperative Blood Recovery on Homologous Blood Transfusion Requirement in Cementless Total Hip Replacement Operation, Journal of American College of Surgeons, pp. 561-567, vol. 180 (May 1995).

Huo, M.D. et al., Oblique Femoral Osteotomy in Cementless Total Hip Arthroplasty, Prospective Consecutive Series With a 3-Year Minimun Follow-up Period, The Journal of Arthroplasty, pp. 310-327, vol. 10, No. 3 (1995).

Huo, M.D. et al., Periprosthetic Femoral Fracture Treatment With an Intramedullary Extension Sleeve, Journal of Orthopaedic Techniques, pp. 191-195, vol. 2, No. 4 (Dec. 1994).

Huo, M.D. et al., Periprosthetic Infection in Total Hip Replacement Management with Temporary Prostheses and Antibiotic-impregnated Cement Between Stages, A Technical Note and Cost Analysis, Journal of Orthopaedic Techniques, pp. 93-101, vol. 2, No. 3, Sep. 1994.

Huo, M.D. et al., Total Hip Arthroplasty Using the Zweymuller Stem Implanted Without Cement, A Prospective Study of Consecutive Patients With Minimum 3-Year Follow-up Period, The Journal of Arthroplasty, pp. 793-799, vol. 10, No. 6 (1995).

Huo, M.D. et al., Total Hip Replacements Done Without Cement After Acetabular Fractures, A 4- to 8-Year Follow-up Study, The Journal of Arthroplasty, pp. 827-831, vol. 14, No. 7, (1999).

Huo, M.D. et al., Total Hip Replacements Using the Ceramic Mittelmeier Prosthesis, Clinical Orthopaedics and Related Research, pp. 143-150, No. 332 (Nov. 1996).

Huo, M.D. et al., Unsatisfactory Results of a First-generation Modular Femoral Stem Implanted Without Cement, A 4- to 9-Year Follow-up Study, The Journal of Arthroplasty, pp. 490-496, vol. 12, No. 5 (1997).

Jokl, M.D. et al., Non-Operative Treatment of Severe Injuries to the Medial and Anterior Cruciate Ligaments of the Knee, The Journal of Bone and Joint Surgery, pp. 741-744, vol. 66-A, No. 5 (Jun. 1984).

Keggi et al., Stabilization of the Spine Using Methylmethacrylate (undated).

Keggi et al., Vertebral Artery Insufficiency Secondary to Trauma and Osteoarthritis of the Cervical Spine, Yale Journal of Biology and Medicine, pp. 471-478, vol. 38 (Apr. 1966).

Keggi, M.D. et al., A Methodology for Studying the Emergency Care of the Trauma Patient: Results of the Yale Trauma Study, Connecticut Medicine, pp. 107-114, vol. 34, No. 2 (Feb. 1970).

Keggi, M.D. et al., Anterior Approach to Total Hip Replacement: Surgical Technique and Clinical Results of Our First One Thousand Cases Using Non-Cemented Prostheses, Yale Journal of Biology and Medicine, vol. 66, pp. 243-246, (1993).

Keggi, M.D. et al., Methylmethacrylate Stabilization of the Cervical Spine, The Journal of Bone and Joint Surgery, pp. 40-46, vol. 66-A, No. 1 (Jan. 1984).

Keggi, M.D. et al., Portable Television in Medicine and Medical Education, Journal of Medical Education, pp. 258-261, vol. 45 (Apr. 1970).

Keggi, M.D. et al., The Anterior Approach to Total Hip Replacement, A Clinical Exhibit (Booth 1477) presented at the 44th Annual Meeting, American Academy of Orthopaedic Surgeons in Las Vegas, Nevada (Feb. 3-8, 1977).

Keggi, M.D., Cementless Ceramic Hip Replacement The Anterior Approach, Masters of Surgery, Glaxo, Inc., Copyright 1985.

Keggi, Strides, Newsletter of the Keggi Orthopaedic Foundation, vol. XII No. 2, Fall 2003.

Keggi, Strides, Newsletter of the Keggi Orthopaedic Foundation, vol. X No. 1, Spring 2001.

Keggi, Two Incision Approach as performed by Kristaps J. Keggi, M.D., printout of Power Point presentation presented at Yale Orthopaedic Alumni in Banff, Jun. 1988.

Kelsey et al., An Epidemiological Study of the Effect of Fluorides in Drinking Water on the Frequency of Slipped Capital Femoral Epiphysis, Yale Journal of Biology and Medicine, pp. 274-285, vol. 44 (Dec. 1971).

Kelsey, Ph.D. et al., The Body Build of Patients with Slipped Capital Femoral Epiphysis, Amer J Dis Child, pp. 276-281, vol. 124 (Aug. 1972).

Kelsey, Ph.D. et al., The Incidence and Distribution of Slipped Capital Femoral Epiphysis in Connecticut and Southwestern United States, The Journal of Bone and Joint Surgery, pp. 1203-1216, vol. 52-A, No. 6 (Sep. 1970).

Kennon, M.D. et al., Anterior Approach THA: Beyond The Minimally Invasive Technique, Keggi Orthopaedic Foundation, Yale University School of Medicine Department of Orthopaedics & Rehabilitation, Joint Implant Surgery and Research Foundation [undated].

Kennon, M.D. et al., Total Hip Arthroplasty Through a Minimally Invasive Anterior Surgical Approach, The Journal of Bone and Joint Surgery, pp. 39-48, vol. 85-A, Supplement 4 [undated].

Kennon, M.D. et al., Total Hip Arthroplasty Using the Minimally Invasive Anterior Surgical Approach, Keggi Orthopaedic Foundation, Joint Implant Surgery & Research Foundation [undated].

Light, M.D. et al., Anterior to Hip Arthroplasty, Clinical Orthopaedics and Related Research © J.B. Lippincott, Co., pp. 255-260, Yale University School of Medicine (May 18, 1980).

Lindsey, M.D. et al., Total Hip Replacement Update: Cement v. Cementless Arthroplasty, Connecticut Medicine, pp. 399-401, vol. 52, No. 7 (Jul. 1988).

McTighe, Ph.D., Editor, A New Era of Minimally Invasive Surgical Approaches for THA, Joint Implant Surgery & Research Foundation, pp. 1-8, Dec. 2002.

Morris, M.D. et al., Clinical and Cineradiographic Evaluation of the Mathisen Ureterosigmoidostomy, Surgery Gynecology & Obstetrics, pp. 481-487, vol. 112, No. 4 (Apr. 1961).

Nagel, M.D. et al., Closer Look at Spinal Lesions, Jama, pp. 103-106, JAMA, vol. 191, No. 12 (Mar. 22, 1965).

Newman, Development of Total Hip Replacement, J.B. Lippincott Company, pp. 13-25 (1971).

Panjabi, Ph.D. et al., Biomechanical Study of Cervical Spine Stabilization with Methylmethacrylate, Spine, pp. 198-203, vol. 10 (1985).

Panjabi, Ph.D. et al., Posterior Spine Stabilization with Methylmethacrylate, Spine, pp. 241-247, vol. 2, No. 4 (Dec. 1977).

Skoff, M.D. et al., Total Hip Replacement in Down's Syndrome, Orthopedics®, pp. 485-489, vol. 10, No. 3, (Mar. 1987).

Skoff, M.D. et al., Total Hip Replacement in the Neuromuscularly Impaired, Orthopaedic Review, pp. 154/65-70/159 vol. XV, No. 3 (Mar. 1986).

Southern, M.D. et al., Unwashed Wound Drainage Blood, What Are We Giving Our Patients?, Clinical Orthopaedics and Related Research, pp. 235-246, No. 320 (1995).

Southwick, M.D. et al., The Normal Cervical Spine, The Journal of Bone and Joint Surgery, pp. 1767-1776, vol. 46-A, No. 8 (Dec. 1964).

* cited by examiner

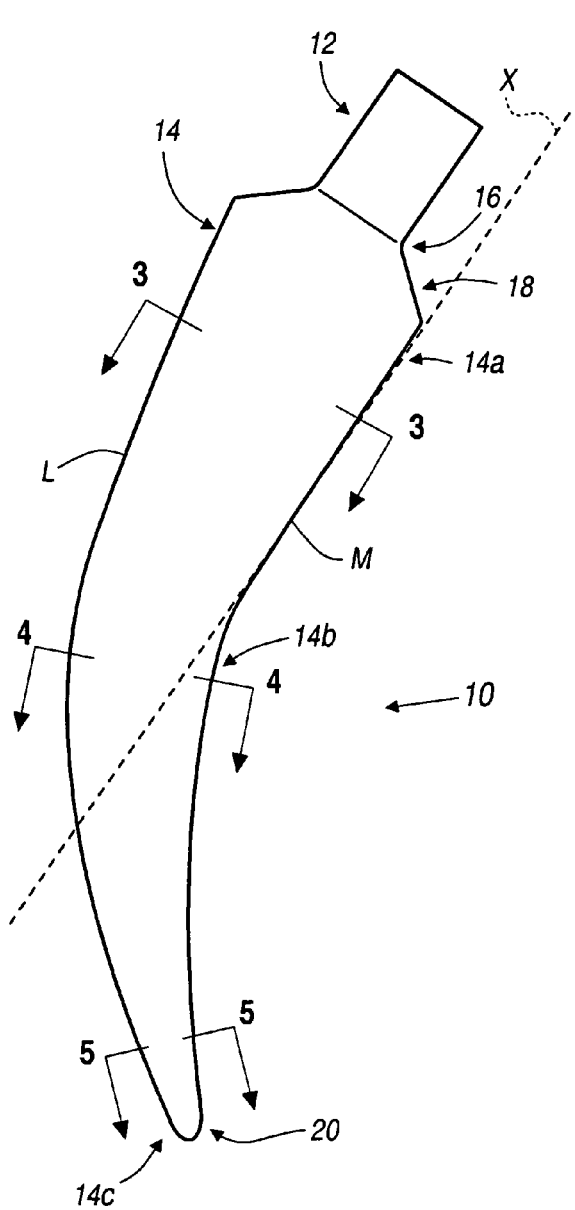
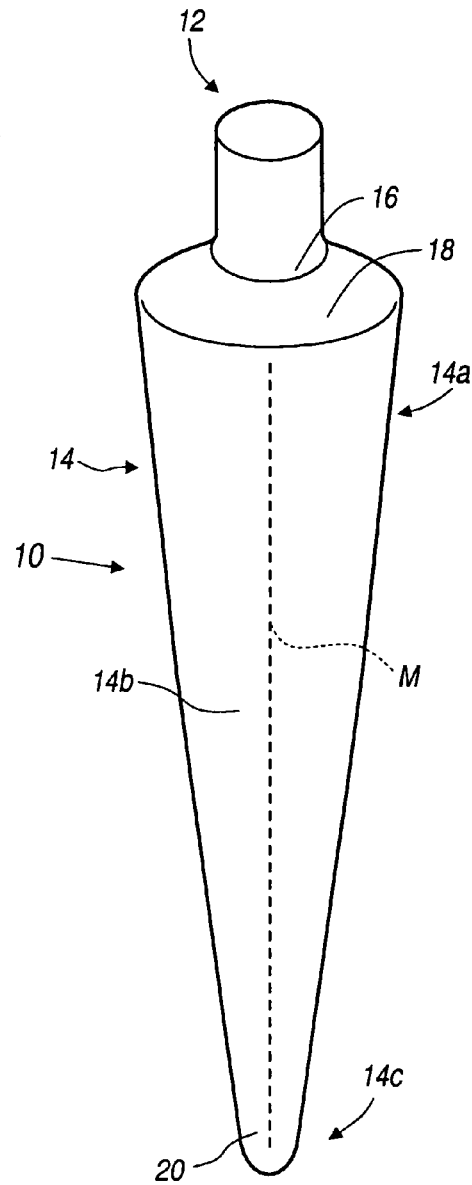
FIG.- 1
FIG.- 1a

METHOD AND APPARATUS FOR PROVIDING A SHORT-STEMMED HIP PROSTHESIS

CROSS-REFERENCE TO RELATED APPLICATIONS

This application is a continuation-in-part of U.S. patent application Ser. No. 10/066,996 filed on Feb. 4, 2002. The disclosure of the above application is incorporated herein by reference.

FIELD OF THE INVENTION

This invention relates generally to a method and apparatus for use in orthopedic surgery and, more particularly, to a method and apparatus for providing a short-stemmed hip prosthesis having a substantially constant radius over at least a portion thereof to ease insertion into bone, a raised lateral lip to resist rotation, and a biplanar taper to conserve bone tissue and promote gradual stress transfer.

BACKGROUND OF THE INVENTION

A natural hip joint may undergo degenerative changes due to a variety of etiologies. When these degenerative changes become so far advanced and irreversible, it may ultimately become necessary to replace a natural hip joint with a prosthetic hip. When implantation of such a hip joint prosthesis becomes necessary, the head of the natural femur is first resected and a cavity is created (e.g., by reaming and/or broaching) within the intramedullary canal of the host femur for accepting the hip prosthesis, typically referred to as a femoral insert. The femoral insert may be inserted and supported within the host femur by cementing the femoral insert within the host femur. Alternatively, the femoral insert may be impacted into the host femur so that it is snugly fit and supported by the host femur.

Due to any number of reasons, however, a small portion of patients that undergo such orthopedic surgical procedures may require subsequent revision surgery to replace the hip prosthesis with a new prosthetic device generally referred to as a revision prosthesis. Because conventional hip replacement procedures typically removes a relatively significant amount of bone tissue from the area surrounding the proximal intramedullary canal, there is less bone and are significant problems associated with securing the revision prosthesis to the remaining femoral structure.

In an effort to overcome this problem, the use of short-stemmed femoral inserts is being described here. By shortening the length of the stem of the femoral insert and placing the prosthesis more proximal to standard primary femoral inserts, the need to remove surrounding bone tissue from the femoral neck and the intramedullary canal is substantially lessened. As a result, significant amounts of bone tissue are available for any subsequent revision procedures and therefore the ability to insert a traditional primary prosthesis as a revision to the short-stemmed femoral insert. This is especially beneficial for younger patients that will most likely require one or more revision prostheses during their lifetime.

Although these short-stemmed femoral inserts have aided somewhat in the preservation of femoral bone tissue, the issues of ease of insertion, prosthesis rotation, loosening, stress shielding, subsidence, and loading remain to be more fully and satisfactorily addressed.

Therefore, there remains a need for a method and apparatus for providing a short-stemmed femoral insert that is easily inserted into the femur, prevents prosthesis rotation, eliminates or lessons the probability of wear debris migration distally, eliminates or at least lessens the probability of stress shielding and subsidence, and provides surface loading as opposed to point loading.

SUMMARY OF THE INVENTION

The present teachings provide a method of implanting at least a stem member of a femoral insert into an intramedullary canal of a femur. The method includes making an anterior incision for accessing the intramedullary canal, and inserting a stem member of the femoral insert into the intramedullary canal through the incision along an arcuate path defined by an arcuate profile of the stem member. The acetabulum can be reamed superiorly through the incision and an acetabular cup can be inserted through the incision.

A more complete appreciation of the present invention and its scope can be obtained from the following detailed description of the invention, the drawings and the appended claims.

BRIEF DESCRIPTION OF THE DRAWINGS

The present invention will become more fully understood from the detailed description and the accompanying drawings, wherein:

FIG. 1 is a front elevational view of a femoral insert, in accordance with one embodiment of the present invention;

FIG. 1A is a side elevational view of the femoral insert depicted in FIG. 1, in accordance with one embodiment of the present invention;

The same reference numerals refer to the same parts throughout the various figures.

DETAILED DESCRIPTION OF THE INVENTION

Figure 2:
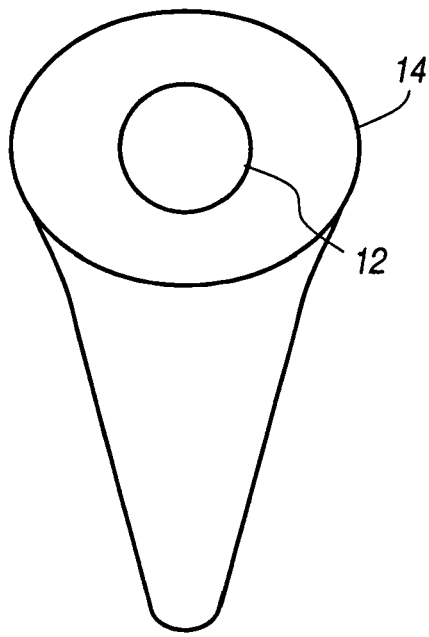
FIG. 2 is a top plan view of the femoral insert depicted in FIG. 1, in accordance with one embodiment of the present invention.
Figure 3:
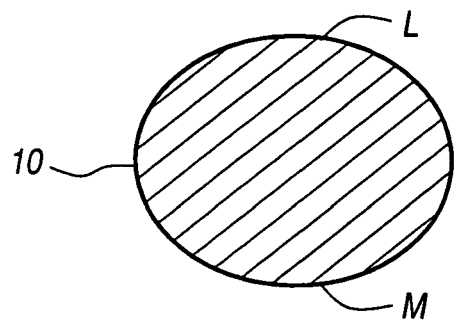
FIG. 3 is a cross-sectional view along line 3-3 of the femoral insert depicted in FIG. 1, in accordance with one embodiment of the present invention.
Figure 4:
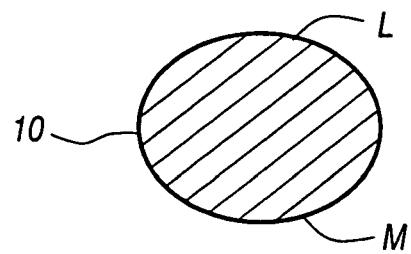
FIG. 4 is a cross-sectional view along line 4-4 of the femoral insert depicted in FIG. 1, in accordance with one embodiment of the present invention.
Figure 5:
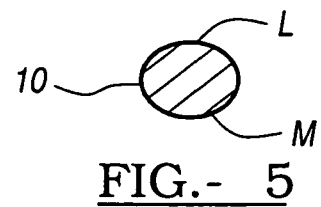
FIG. 5 is a cross-sectional view along line 5-5 of the femoral insert depicted in FIG. 1, in accordance with one embodiment of the present invention.
Figure 6:
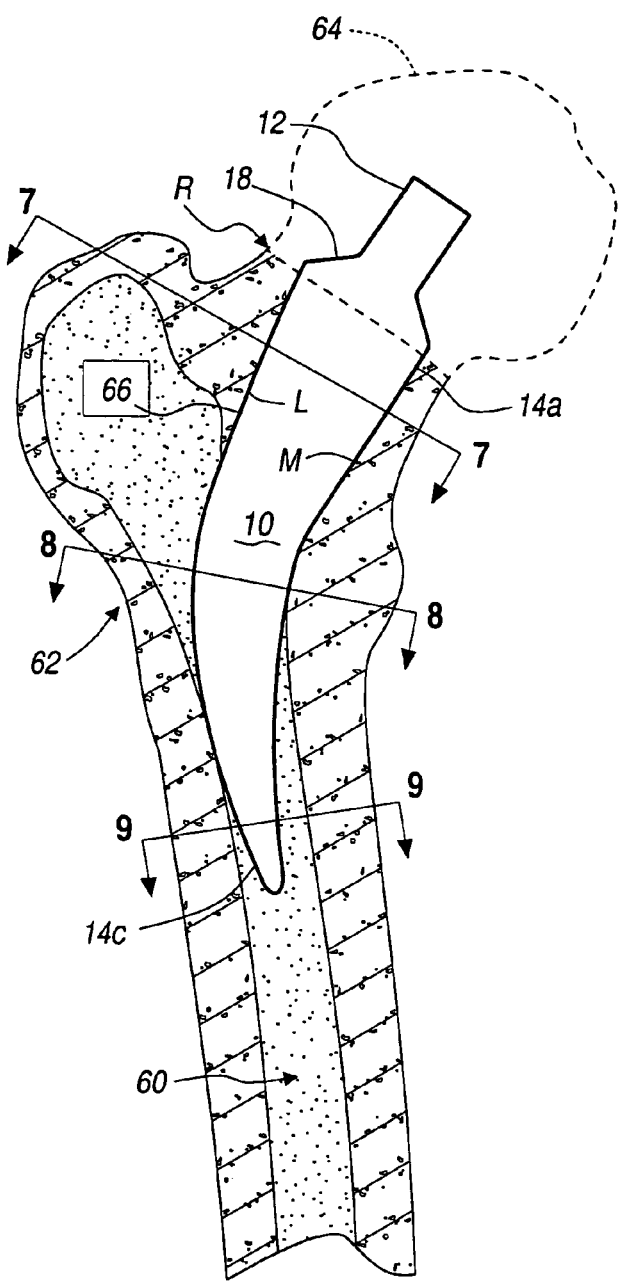
FIG. 6 is a partial cross-sectional view of the femoral insert depicted in FIG. 1 that has been implanted into an intramedullary canal of a femur, in accordance with one embodiment of the present invention.
Figure 7:
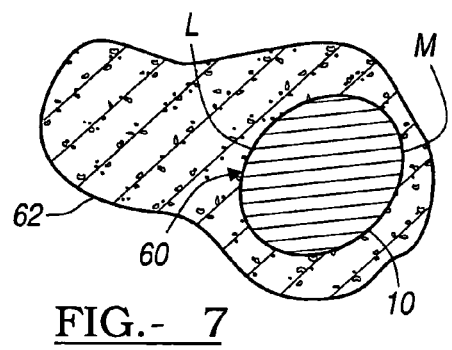
FIG. 7 is a cross-sectional view along line 7-7 of the femoral insert depicted in FIG. 6, in accordance with one embodiment of the present invention.
Figure 8:
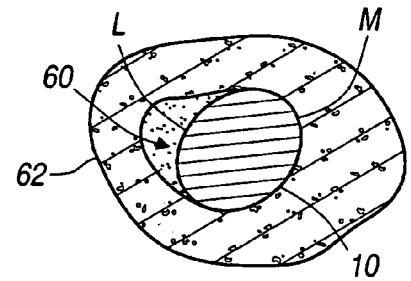
FIG. 8 is a cross-sectional view along line 8-8 of the femoral insert depicted in FIG. 6, in accordance with one embodiment of the present invention.
Figure 9:
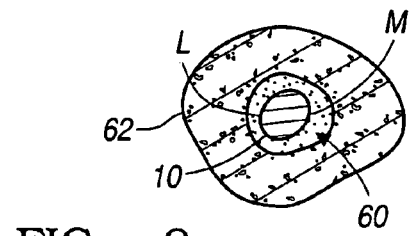
FIG. 9 is a cross-sectional view along line 9-9 of the femoral insert depicted in FIG. 6, in accordance with one embodiment of the present invention.
Figure 10:
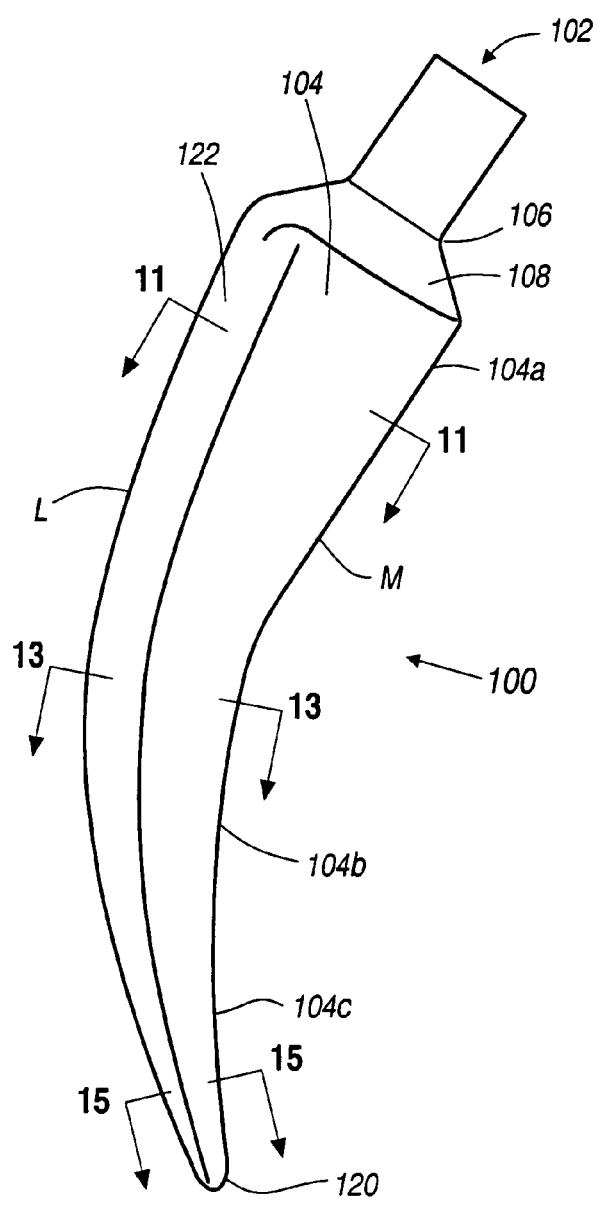
FIG. 10 is a front elevational view of an alternative femoral insert, in accordance with an alternative embodiment of the present invention.
Figure 10A:
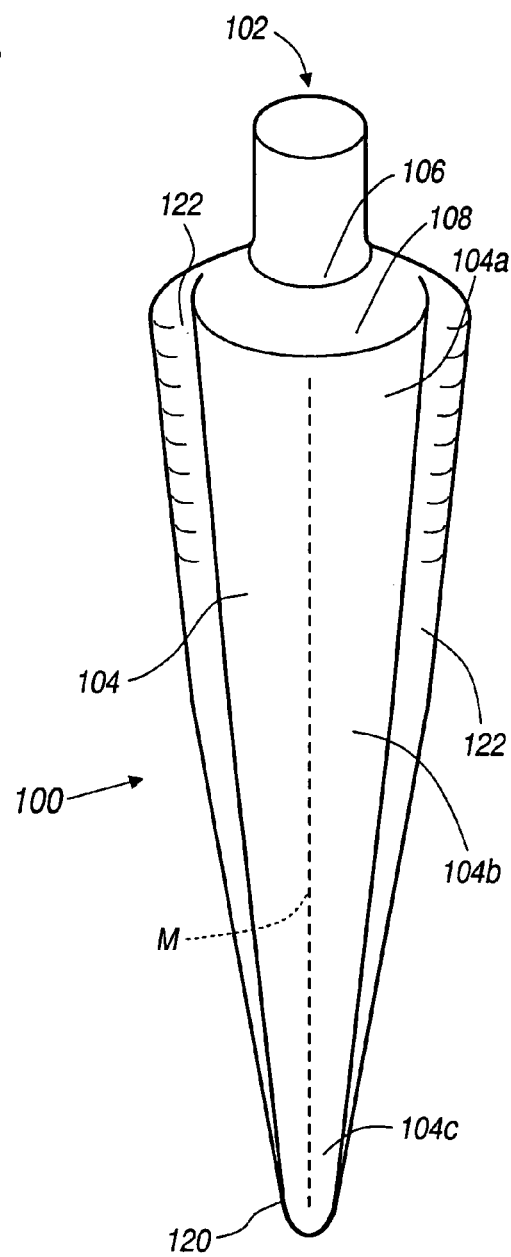
FIG. 10A is a side elevational view of the femoral insert depicted in FIG. 10, in accordance with an alternative embodiment of the present invention.
Figure 11:
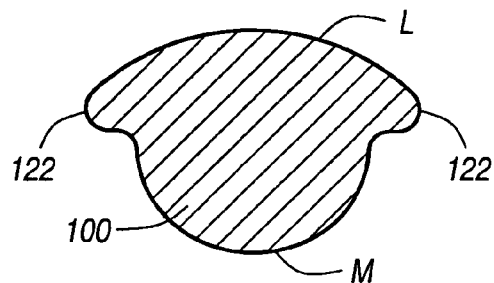
FIG. 11 is a cross-sectional view along line 11-11 of the femoral insert depicted in FIG. 10, in accordance with an alternative embodiment of the present invention.
Figure 12:
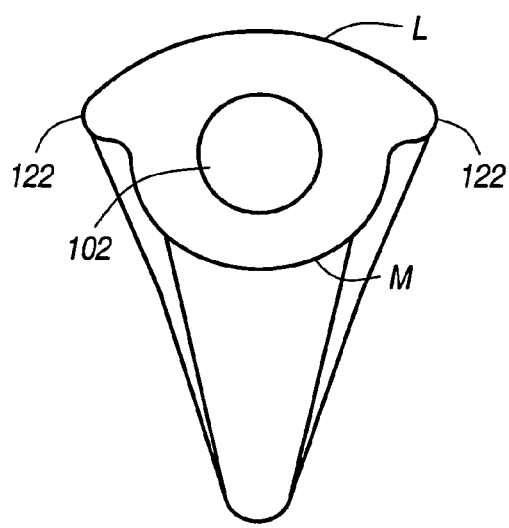
FIG. 12 is a top plan view of the femoral insert depicted in FIG. 10, in accordance with an alternative embodiment of the present invention.
Figure 13:
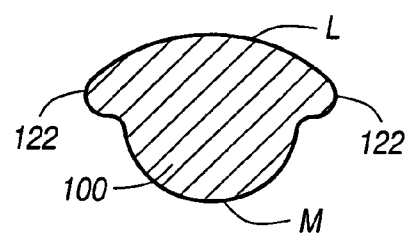
FIG. 13 is a cross-sectional view along line 13-13 of the femoral insert depicted in FIG. 10, in accordance with an alternative embodiment of the present invention.
Figure 14:
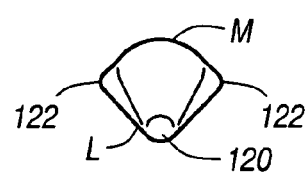
FIG. 14 is a bottom plan view of the femoral insert depicted in FIG. 10, in accordance with an alternative embodiment of the present invention.
Figure 15:
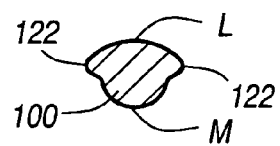
FIG. 15 is a cross-sectional view along line 15-15 of the femoral insert depicted in FIG. 10, in accordance with an alternative embodiment of the present invention.

The following description of the preferred embodiments concerning a method and apparatus for providing a short-stemmed femoral insert for use in orthopedic surgical procedures are merely exemplary in nature and are not intended to limit the invention or its application or uses. Moreover, while the present invention is described in detail below with reference to performing a primary type implantation procedure, it will be appreciated by those skilled in the art that the present invention is clearly not limited to only primary type orthopedic surgical procedures and may be used with various other orthopedic surgical procedures as well, including revision type orthopedic surgical procedures.

Referring to FIGS. 1-5, there is generally shown a femoral insert 10, in accordance with one embodiment of the present invention. The femoral insert 10 is preferably comprised of a biocompatible material, such as titanium alloys, stainless steel, chrome-cobalt alloys, and the like. The femoral insert 10 includes a trunion portion 12 and a stem portion 14. At the distal end 16 of the trunion portion 12, the stem portion 14 includes a tapered proximal portion 18, such that a taper exists in the anterior-posterior (AP) plane. The taper begins at the proximal portion 18 and extends downwardly towards the distal end portion 20 of the stem portion 14.

The stem portion 14 is approximately 95 mm long and thus would be considered to fall into the afore-mentioned short-stemmed femoral insert category. However, stem portions having lengths in the range of about 75 mm to about 105 mm are envisioned, as well. The use of a short stem reduces the incidence of thigh pain typically associated with loading of a relatively long-stemmed femoral implant. Additionally, the short stem allows for the conservation of bone tissue in and around the femoral neck and intramedullary canal, and accordingly, the present invention can be used in primary type implantation procedures, as well as revision type implantation procedures.

The stem portion 14 is actually comprised of three distinct sections: a proximal section 14A, a middle section 14B, and a distal section 14C. It is envisioned that the stem portion 14 can be defined by a single region with a varying radius. As best seen in FIGS. 2-5, the cross-section has a generally elliptical shape. Those skilled in the art will understand that the cross-section can also be circular or another appropriate shape.

The proximal section 14A preferably includes lateral and medial surfaces, L and M, respectively, having an equal, or at least substantially constant equal radius, i.e., as the cross-sectional area of the stem 14 decreases from the proximal portion 18 to the distal end portion 20, the radius of the lateral surface L is equal to, or at least substantially equal to, the radius of the medial surface M. The proximal section 14A preferably includes anterior and posterior surfaces, A and P, respectively, having a equal, or at least substantially equal taper angle, i.e. as the diameter of the stem 14 decreases from the proximal portion 18 to the distal portion 20. The benefit of the equal constant radius feature is that it allows for easier insertion of the femoral insert and lateral surface loading (e.g., against the lateral surface of the cortical bone of the intramedullary canal), as opposed to point loading, as is the case for conventional short-stemmed femoral inserts. The benefit of the taper feature is that it allows for ease of insertion and better off-loading of the implant to the host femur. This allows the femoral insert 10 to better tolerate and withstand the loading forces typically experienced by femoral inserts, for example, during walking, running, or jumping by the patient.

The outer surface of the proximal section 14A may be provided with an optional cicumferential porous coating (not shown) so as to facilitate the in-growth of new bone tissue therein. The porous coating can be a variety of applications including, but not limited to titanium plasma spray, sintered beads, titanium mesh, etc. The optional porous coating can also be applied at varying levels thus not being limited to only the proximal section 14A, but also 14C.

The distal section 14C, is a section where the respective radii of the lateral surface L and medial surface M of the proximal section 14A converge together towards the distal end portion 20. However, instead of converging together to form a point along a longitudinal axis X of the stem portion 14, the respective radii converge so as to form a distal arc taper portion 14C. The benefit of the distal arc taper section 14C is that it prevents subsidence of the femoral insert 10 and prevents point loading of the distal end of the femoral insert. The radii of the lateral surface L and medial surface M of the stem 14 substantially converge along the distal portion 14C so as to form a substantially arcuate configuration tangential to the proximal portion 14A.

The implantation of the femoral insert 10 will now be described in connection with a primary type implantation procedure. However, as previously mentioned, the femoral insert 10 is equally useful for revision type implantation procedures, as well.

Referring to FIGS. 6-9, the femoral implant 10 is shown in its fully and properly seated position within the intramedullary canal 60 of a patient's femur 62. The femur head 64, shown in dashed line, has been previously resected and the proximal portion 66 of the intramedullary canal 60 has been properly broached and prepared for the femoral insert 10. It should be noted that there is generally no need for reaming with the femoral insert 10 of the present invention.

The femoral insert 10 is very easily inserted into the intramedullary canal 60 and may then be pressed further into the intramedullary canal 60 so as to be snuggly and securely retained therein, as is known in the art. There is generally no need for bone cement; however, bone cement may be used, if clinically indicated.

It will be noted that the medial surface M of the proximal portion 14A abuts against the medial surface of the proximal portion 66 of the intramedullary canal (femoral neck) 60, i.e., against the cortical bone tissue. It will also be noted that the lateral surface L of the mid portion (slightly distal to FIG. 8) abuts against the lateral surface of the intramedullary canal, i.e., against the cortical bone tissue. Thus, the loading of the femoral insert 10 is surface loading as opposed to point loading. This feature greatly enhances the ability of the femoral insert 10 to withstand the significant stresses and loads placed upon it by the patient's various movements. Further, the loading characteristics of the femoral insert 10 also aids in the prevention and/or lessening of stress shielding and thigh pain. Additionally, it will be noted that other areas of surface loading are available as well, such as, but not limited to the femoral neck and calcar region, as well as the femoral head and acetabulum region.

It will also be noted that the distal arc taper section 14C extends towards the medial surface of the intramedullary canal 60, and thus prevents subsidence of the femoral insert 10. In addition, this allows for variations in placement of the femoral insert without the incidence of point loading.

Another feature of the femoral insert 10 is that the proximal portion 18 is placed above the typical resection level R of typical primary and other short-stemmed femoral inserts. This allows less bone to be removed and greater fixation of the femoral insert in the femoral neck thereby leaving more bone if a revision operation is required at some point. This also allows for a smaller incision to be utilized for a more bone conservative treatment of the disease.

In accordance with an alternative embodiment of the present invention, a bilateral radial lip is provided on the entire lateral surface of the stem portion of the femoral insert. Without being bound to a particular theory of the operation of the present invention, it is believed that the bilateral radial lip prevents the unintended rotation of the femoral insert upon implantation within the intramedullary canal and throughout loading of the femoral insert after implantation.

Referring to FIGS. 10-15, there is generally shown an alternative femoral insert 100, in accordance with an alternative embodiment of the present invention. The femoral insert 100 is also comprised of a biocompatible material, such as titanium alloys, stainless steel, chrome-cobalt alloys, and the like. As with the previously described embodiment, the femoral insert 100 includes a trunion portion 102 and a stem portion 104. At the distal end 106 of the trunion portion 102, the stem portion 104 includes a tapered proximal portion 108, such that a taper exists in the anterior-posterior (AP) plane. The taper begins at the proximal portion 108 and extends downwardly towards the distal end portion 120 of the stem portion 104. Again, there is the feature of a constant equal or substantially equivalent radius between the lateral surface L and the medial surface M of the femoral insert 100. While the stem portion 104 is shown comprised of three distinct sections: a proximal section 104A, an intermediate transition section 104B, and a distal section 104C. It is envisioned that the stem portion 104 can be formed of a single distal converging arc taper from the distal end 106 of the trunion portion 102 to the distal end portion 120. Again, the outer surface of the proximal section 104A may be provided with an optional porous coating (not shown) so as to facilitate the in-growth of new bone tissue therein.

However, the primary difference between the alternative embodiment and the embodiment depicted in FIGS. 1-9 is the presence of a bilateral lip member 122 extending along the lateral surface L of the proximal section 104A of the stem 104. The bilateral lip member 122 preferably gradually diminishes in diameter as it approaches the end of the distal converging arc taper section 104C. The actual radius of the lateral surface remains constant from the proximal section 104A to the intermediate transition section 104B. Distal to the transition section the radius of lateral surface decreases allowing the lip to gradually blend into the distal section 104C ending at 120.

The stem portion 104 is approximately 95 mm long and thus would be considered to fall into the afore-mentioned short-stemmed femoral insert category. However, stem portions in the range of about 75 mm to about 105 mm are envisioned, as well.

The implantation of the femoral insert 100 will now be described in connection with a primary type implantation procedure. However, as previously mentioned, the femoral insert 100 is equally useful for revision type implantation procedures, as well.

Figure 16:
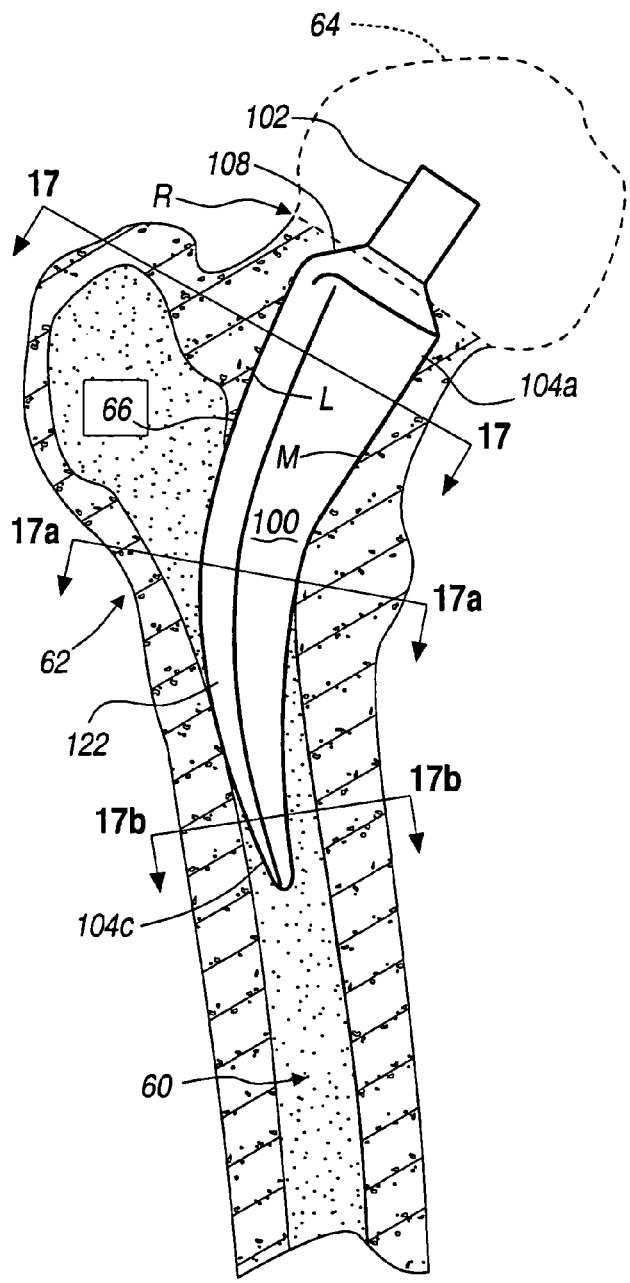
FIG. 16 is a partial cross-sectional view of the femoral insert depicted in FIG. 10 that has been implanted into an intramedullary canal of a femur, in accordance with an alternative embodiment of the present invention.
Figure 17:
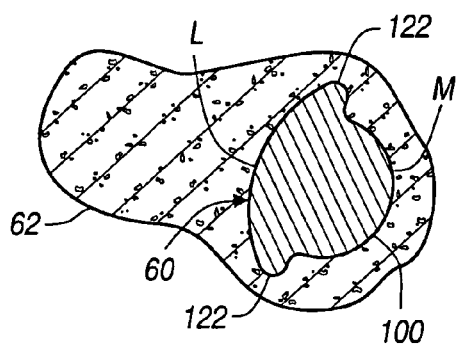
FIG. 17 is a cross-sectional view along line 17-17 of the femoral insert depicted in FIG. 16, in accordance with an alternative embodiment of the present invention.
Figure 17A:
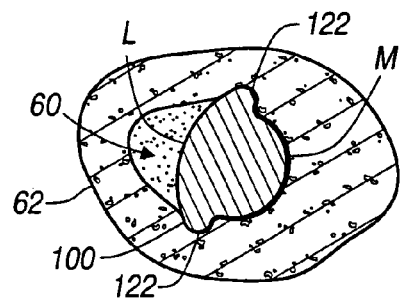
FIG. 17A is a cross-sectional view along line 17A-17A of the femoral insert depicted in FIG. 16, in accordance with an alternative embodiment of the present invention.
Figure 17B:
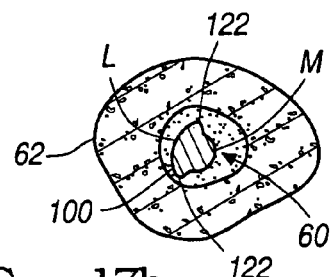
FIG. 17B is a cross-sectional view along line 17B-17B of the femoral insert depicted in FIG. 16, in accordance with an alternative embodiment of the present invention.
Figure 18:
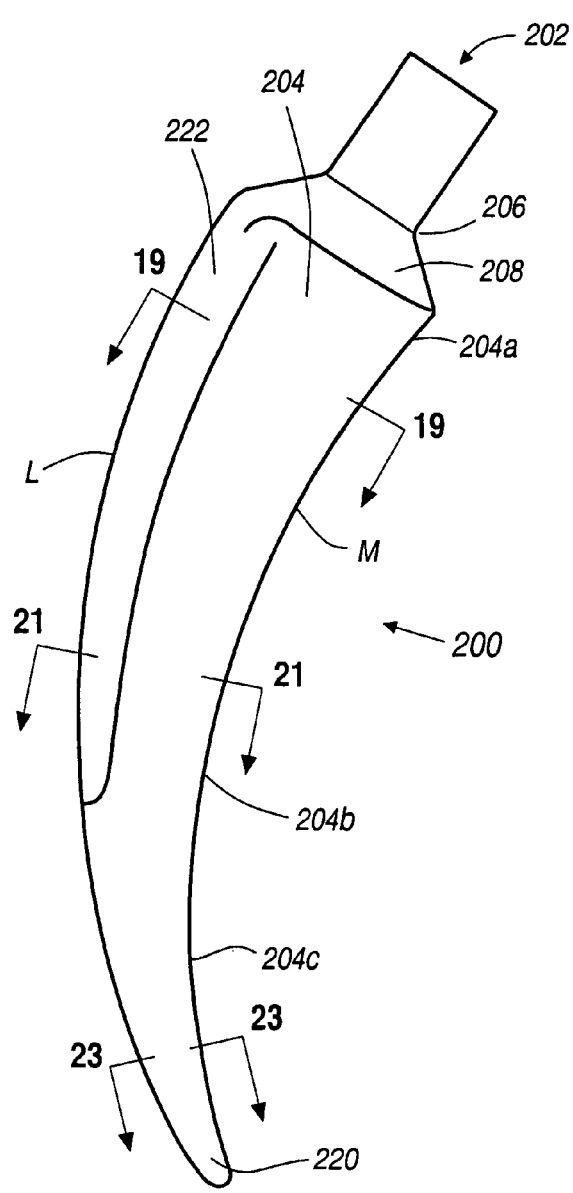
FIG. 18 is a front elevational view of a second alternative femoral insert, in accordance with a second alternative embodiment of the present invention.
Figure 18A:
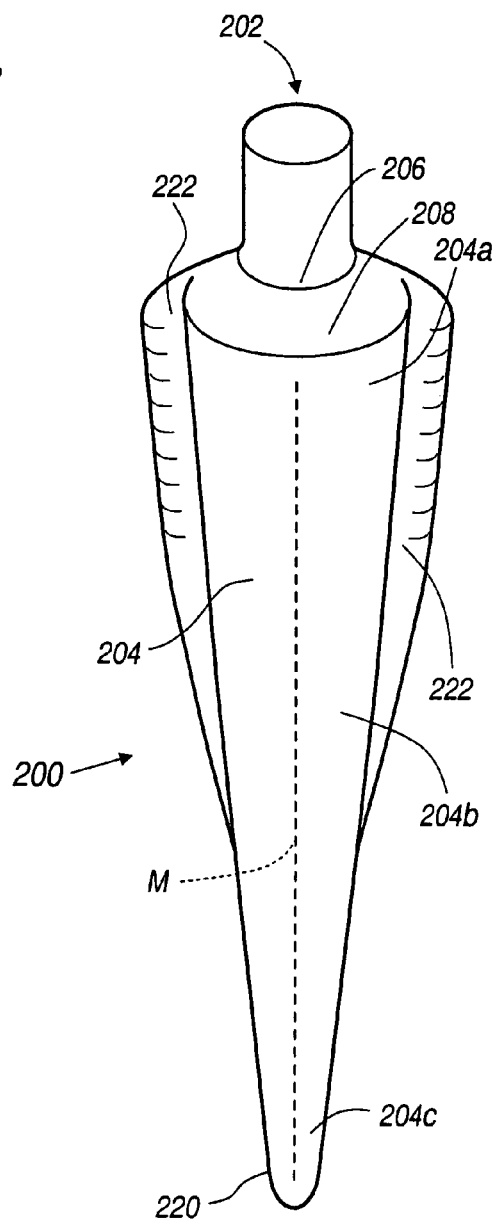
FIG. 18A is a side elevational view of the femoral insert depicted in FIG. 18, in accordance with a second alternative embodiment of the present invention.
Figure 19:
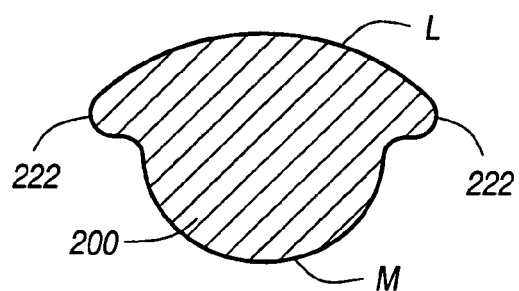
FIG. 19 is a cross-sectional view along line 19-19 of the femoral insert depicted in FIG. 18, in accordance with a second alternative embodiment of the present invention.
Figure 20:
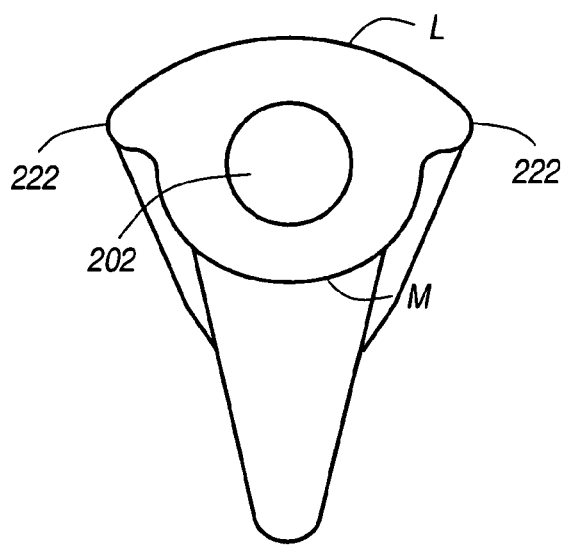
FIG. 20 is a top plan view of the femoral insert depicted in FIG. 18, in accordance with a second alternative embodiment of the present invention.
Figure 21:
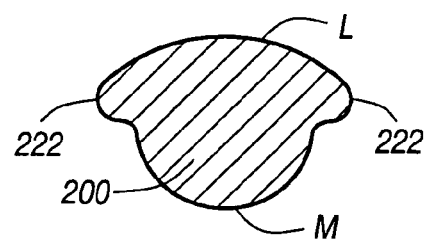
FIG. 21 is a cross-sectional view along line 21-21 of the femoral insert depicted in FIG. 18, in accordance with a second alternative embodiment of the present invention.
Figure 22:
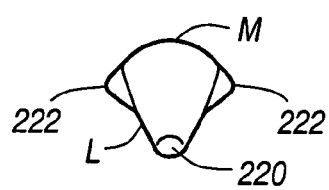
FIG. 22 is a bottom plan view of the femoral insert depicted in FIG. 18, in accordance with a second alternative embodiment of the present invention.
Figure 23:
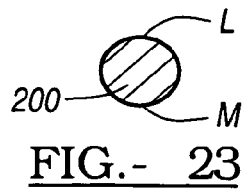
FIG. 23 is a cross-sectional view along line 23-23 of the femoral insert depicted in FIG. 18, in accordance with a second alternative embodiment of the present invention.

Referring to FIGS. 16-17B, the femoral implant 100 is shown in its fully and properly seated position within the intramedullary canal 60 of a patient's femur 62. The femur head 64, shown in dashed line, has been previously resected and the proximal portion 66 of the intramedullary canal 60 has been properly broached and prepared for the femoral insert 100. It should be noted that there is generally no need for reaming with the femoral insert 100 of the present invention and that there is no need to enter a preparation device into the femoral canal (diaphyseal) region according to standard primary femoral insert surgical technique.

The femoral insert 100 is very easily inserted into the intramedullary canal 60 and may then be pressed further into the intramedullary canal 60 so as to be snuggly and securely retained therein, as is known in the art. There is generally no need for bone cement; however, bone cement may be used, if clinically indicated.

It will be noted that the lateral bilateral lip members 122 of the proximal portion 104A abuts against the lateral surface of the proximal portion 66 of the intramedullary canal 60, i.e., against the cortical bone tissue. Thus, providing rotational stability of the implant during loading of the femoral insert 100. In addition, it will be noted that the medial surface M of the proximal portion 104A abuts against the medial surface of the proximal portion 66 of the intramedullary canal (femoral neck), i.e., against the cortical bone tissue. It will also be noted that the lateral surface L of the mid portion (slightly distal to FIG. 17A) abuts against the lateral surface of the intramedullary canal, i.e., against the cortical bone tissue. This feature greatly enhances the ability of the femoral insert 100 to withstand the significant stresses and loads placed upon it by the patient's various movements. Further, the loading characteristics of the femoral insert 100 also aids in the prevention and/or lessening of stress shielding and thigh pain. Additionally, it will be noted that other areas of surface loading are available as well, such as, but not limited to the femoral neck and calcar region, as well as the femoral head and acetabulum region.

It will also be noted that the distal arc taper section 104C extends towards the medial surface of the medial surface of the intramedullary canal 60, and thus prevents subsidence of the femoral insert 100 and allows variations in stem placement without undergoing point loading.

In accordance with another alternative embodiment of the present invention, a bilateral radial lip is provided on only a portion of the lateral surface of the stem portion of the femoral insert, as opposed to the entire lateral surface. Again, without being bound to a particular theory of the operation of the present invention, it is believed that the bilateral radial lip prevents the unintended rotation of the femoral insert upon implantation within the intramedullary canal and during loading of the femoral insert once implanted.

Referring to FIGS. 18-23, there is generally shown a second alternative femoral insert 200, in accordance with an alternative embodiment of the present invention. The femoral insert 200 is also comprised of a biocompatible material, such as titanium alloys, stainless steel, chrome-cobalt alloys, and the like. As with the previously described alternative embodiment, the femoral insert 200 includes a trunion portion 202 and a stem portion 204. The stem portion 204 includes a curvature from the distal end 206 to distal end 220. The curvature begins at the proximal portion 208 and extends downwardly towards the distal end portion 220 of the stem portion 204 and has a constant or substantially equivalent equal radius between the lateral surface L and the medial surface M of the femoral insert 200. Additionally, the stem portion 204 is comprised of three distinct sections: a proximal section 204A, an intermediate transition section 204B, and a distal section 204C. Again, the outer surface of the proximal section 204A may be provided with an optional circumferential porous coating (not shown) or the like so as to facilitate the in-growth of new bone tissue therein.

However, the primary difference between the second alternative embodiment and the embodiment depicted in FIGS. 10-17B is the presence of a bilateral lip member 222 extending along only a portion of the lateral surface L of the proximal section 204A of the stem 204 and the constant curvature. The bilateral lip member 222 preferably gradually diminishes in diameter as it approaches the intermediate transition section 204B and is completely absent as it approaches the end of the distal section 104C. It is envisioned that any of the embodiments can have the constant curvature as opposed to the tapered proximal end.

The stem portion 204 is approximately 95 mm long and thus would be considered to fall into the afore-mentioned short-stemmed femoral insert category. However, stem portions in the range of about 75 mm to about 105 mm are envisioned, as well.

The implantation of the femoral insert 200 will now be described in connection with a primary type implantation procedure. However, as previously mentioned, the femoral insert 200 is equally useful for revision type implantation procedures, as well.

Figure 24:
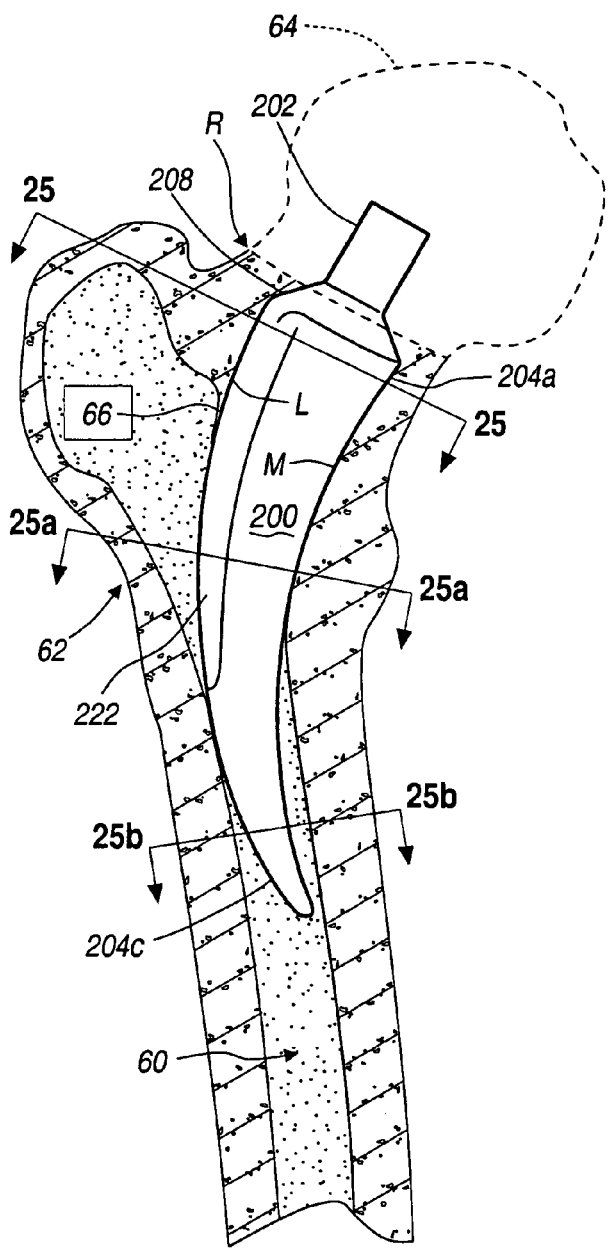
FIG. 24 is a partial cross-sectional view of the femoral insert depicted in FIG. 18 that has been implanted into an intramedullary canal of a femur, in accordance with a second alternative embodiment of the present invention.
Figure 25:
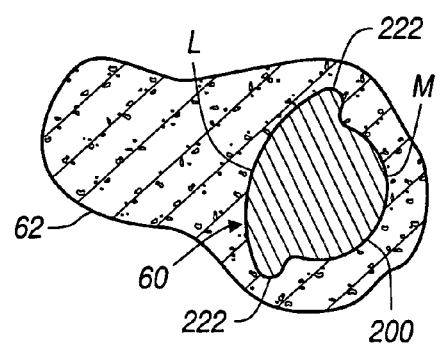
FIG. 25 is a cross-sectional view along line 25-25 of the femoral insert depicted in FIG. 24, in accordance with a second alternative embodiment of the present invention.
Figure 25A:
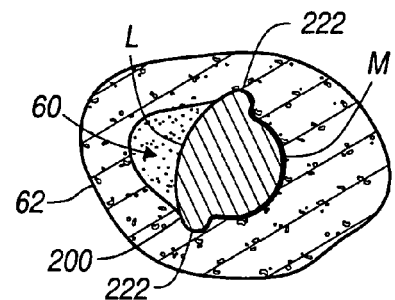
FIG. 25A is a cross-sectional view along line 25A-25A of the femoral insert depicted in FIG. 24, in accordance with a second alternative embodiment of the present invention.
Figure 25B:
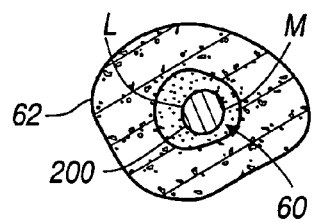
FIG. 25B is a cross-sectional view along line 25B-25B of the femoral insert depicted in FIG. 24, in accordance with a second alternative embodiment of the present invention.

Referring to FIGS. 24-25B, the femoral implant 200 is shown in its fully and, properly seated position within the intramedullary canal 60 of a patient's femur 62. The femur head 64, shown in dashed line, has been previously removed and the proximal portion 66 of the intramedullary canal 60 has been properly broached and prepared for the femoral insert 200. It should be noted that there is generally no need for reaming with the femoral insert 200 of the present invention.

The femoral insert 200 is very easily inserted into the intramedullary canal 60 and may then be pressed further into the intramedullary canal 60 so as to be snuggly and securely retained therein, as is known in the art. There is generally no need for bone cement; however, bone cement may be used, if clinically indicated.

It will be noted that the bilateral radial lip members 222 of the proximal portion 204A abuts against the lateral surface of the proximal portion 66 of the intramedullary canal 60, i.e., against the cortical bone tissue. Thus, providing rotational stability of the implant during loading of the femoral insert 200. In addition, it will be noted that the medial surface M of the proximal portion 204A abuts against the medial surface of the proximal portion 66 of the intramedullary canal (femoral neck), i.e., against the cortical bone tissue. It will also be noted that the lateral surface L of the mid portion (slightly distal to FIG. 25A) abuts against the lateral surface of the intramedullary canal, i.e., against the cortical bone tissue. This feature greatly enhances the ability of the femoral insert 200 to withstand the significant stresses and loads placed upon it by the patient's various movements. Further, the loading characteristics of the femoral insert 200 also aid in the prevention and/or lessening of stress shielding and thigh pain. Additionally, it will be noted that other areas of surface loading are available as well, such as, but not limited to the femoral neck and calcar region, as well as the femoral head and acetabulum region.

It will also be noted that the distal section 204C extends towards the medial surface of the intramedullary canal 60, and thus prevents subsidence of the femoral insert 200 and allow various orientations of the femoral insert without point loading.

Figure 26:
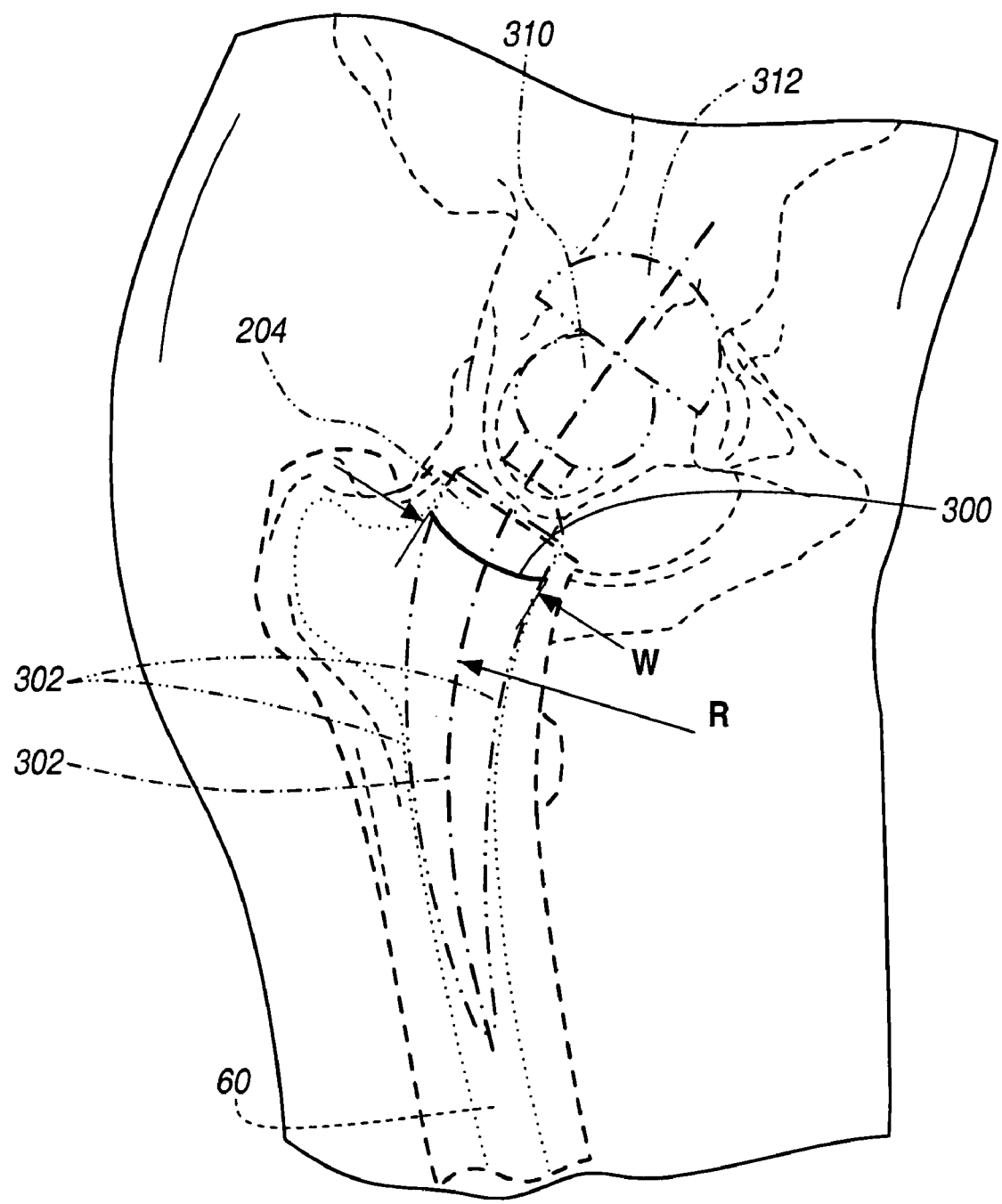
FIG. 26 is side view of a femur rotated 90° from the anatomical position illustrating an anterior incision for implanting at least one femoral insert shown in phantom.
Figure 27:
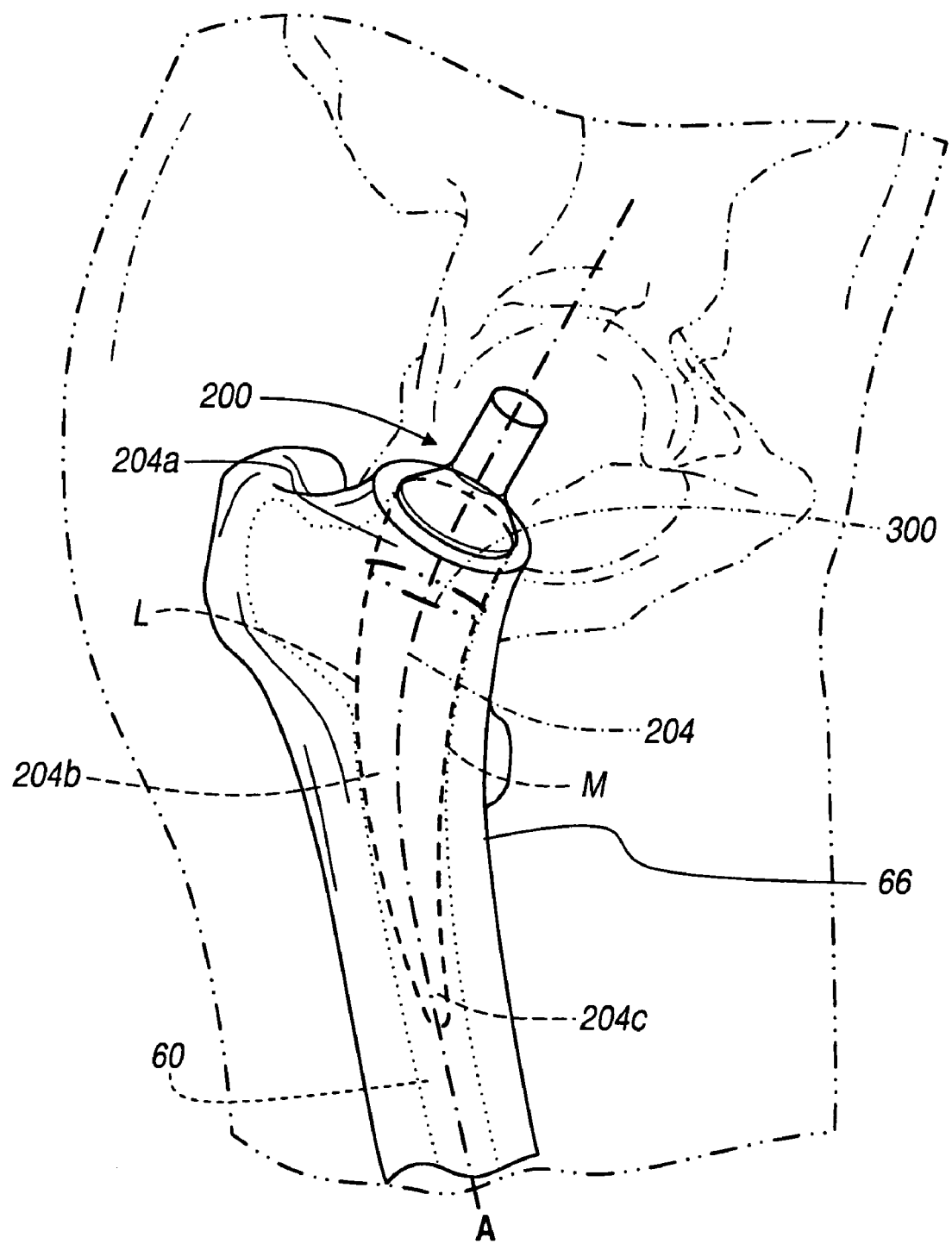
FIG. 27 is a side view of a femoral insert implanted through a small incision in the femur along an arcuate path according to the present teachings.

Referring to FIGS. 26-30, the stem portion 204 of the femoral insert 200 or the femoral inserts of any of the other embodiments described above can be easily implanted into the intramedullary canal 60 using a minimally invasive procedure through a small incision 300, such as an anterior incision, along an arcuate path, generally referenced at 302. The anterior incision is generally located over the neck region of the femur when the patient is supine on the operating table. The incision 300 is also generally made transverse to the neck having a length of about ten centimeters. The incision is, therefore, oriented at about 90° relative to arcuate axis "A" along the intramedullary canal. Upon making the incision 300 through the tissue over the neck of the femur, the neck is generally resected to remove the natural femoral head. This provides access to the intramedullary canal of the femur. The arcuate path 302 is defined by the profile of the stem 204, which has a curvature that begins at the proximal portion 208 and extends downwardly towards the distal end portion 220 of the stem portion 204 and it can have a constant radius R or a substantially equal radius between the lateral surface L and the medial surface M of the femoral insert 200. The radius R can be from about 2.5 inches to 3.5 inches. Referring to FIG. 27, the medial surface M of the proximal portion 204A of the stem 204 abuts against the medial surface of the proximal portion 66 of the intramedullary canal and the lateral surface L of the mid portion 204B of the stem 204 abuts against the lateral surface of the intramedullary canal 60. Additionally, the lateral surface L of the distal portion 204C of the stem 204 can abut lateral surface of the distal portion of the intramedullary canal.

Figure 28:
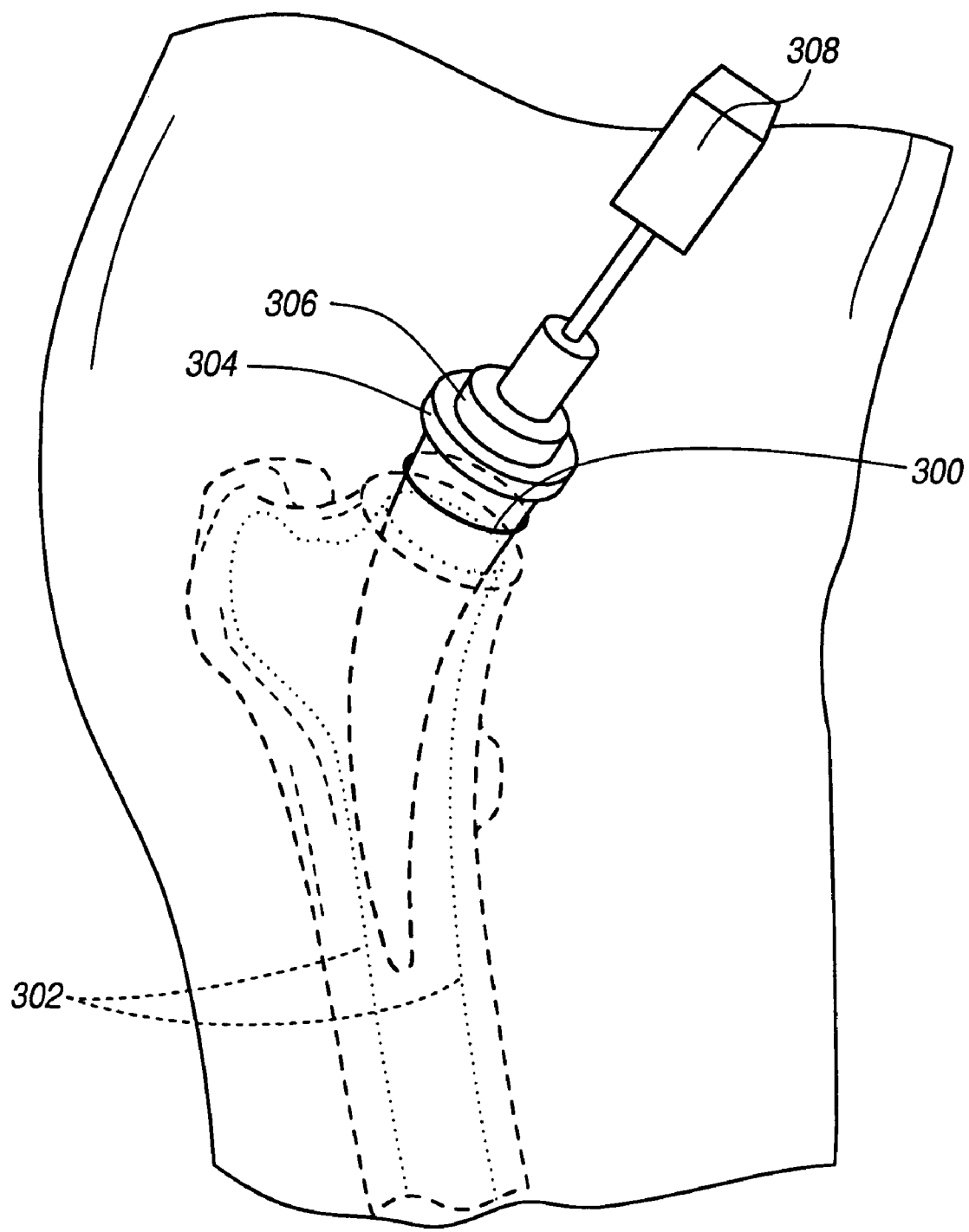
FIG. 28 is side view of a femur illustrating a preparation instrument inserted through an incision along an arcuate path according to the present teachings.

The arcuate profile of the stem portion 204 facilitates the insertion of the stem portion 204 through the small incision 300, and into the femur. The width "W" of the incision 302 generally is sized to mate with the widest dimension of the stem 204. The constant radius of the arcuate path 302 allows an insertion guide 304 outside the incision 300 to guide preparation cutting and shaping instruments 306, such as curved broaches, awls and reamers, that have equal constant radius along the arcuate path 302, as shown in FIG. 28. Known image guidance methods and devices, generally referenced at 308, may also be used to position the insertion guide 304 onto the femur, thereby allowing the incision 300 to be at nearly 90 degrees relative to the arcuate axis A.

Figure 30:
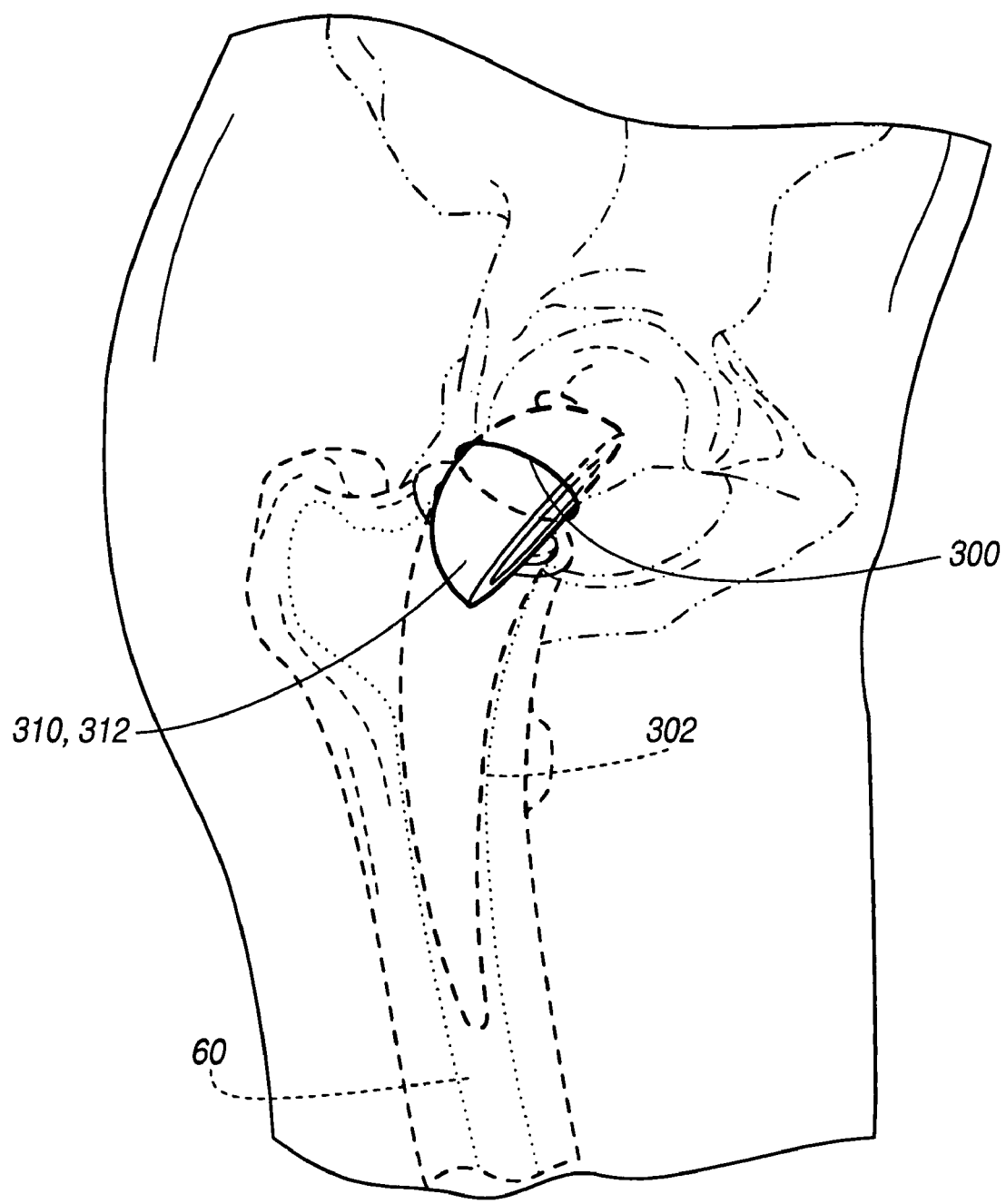
FIG. 30 a side view of an acetabular component partially inserted through a small incision in the femur according to the present teachings.

Referring to FIGS. 26 and 30, a femoral head 310 is attached integrally or modularly with the stem 204 using a Morse taper or other connection device. The femoral head 310 can also be inserted inferiorly through the incision 300. Because of the natural stretchability of the tissues associated with the incision 300, the width of the incision can accommodate the femoral head 310 although the width of the femoral head 310 may be somewhat larger than the width of the incision. Thus, the arcuate constant radius profile of the stem member 204 reduces the width W of the incision. Should the acetabulum need replacement, an acetabular cup 312 can be inserted superiorly through the incision 300, which can have a longer width sized to accommodate the acetabular cup 312. Preparation instruments 306 for the acetabulum can also be inserted superiorly through the incision 300.

Figure 29:
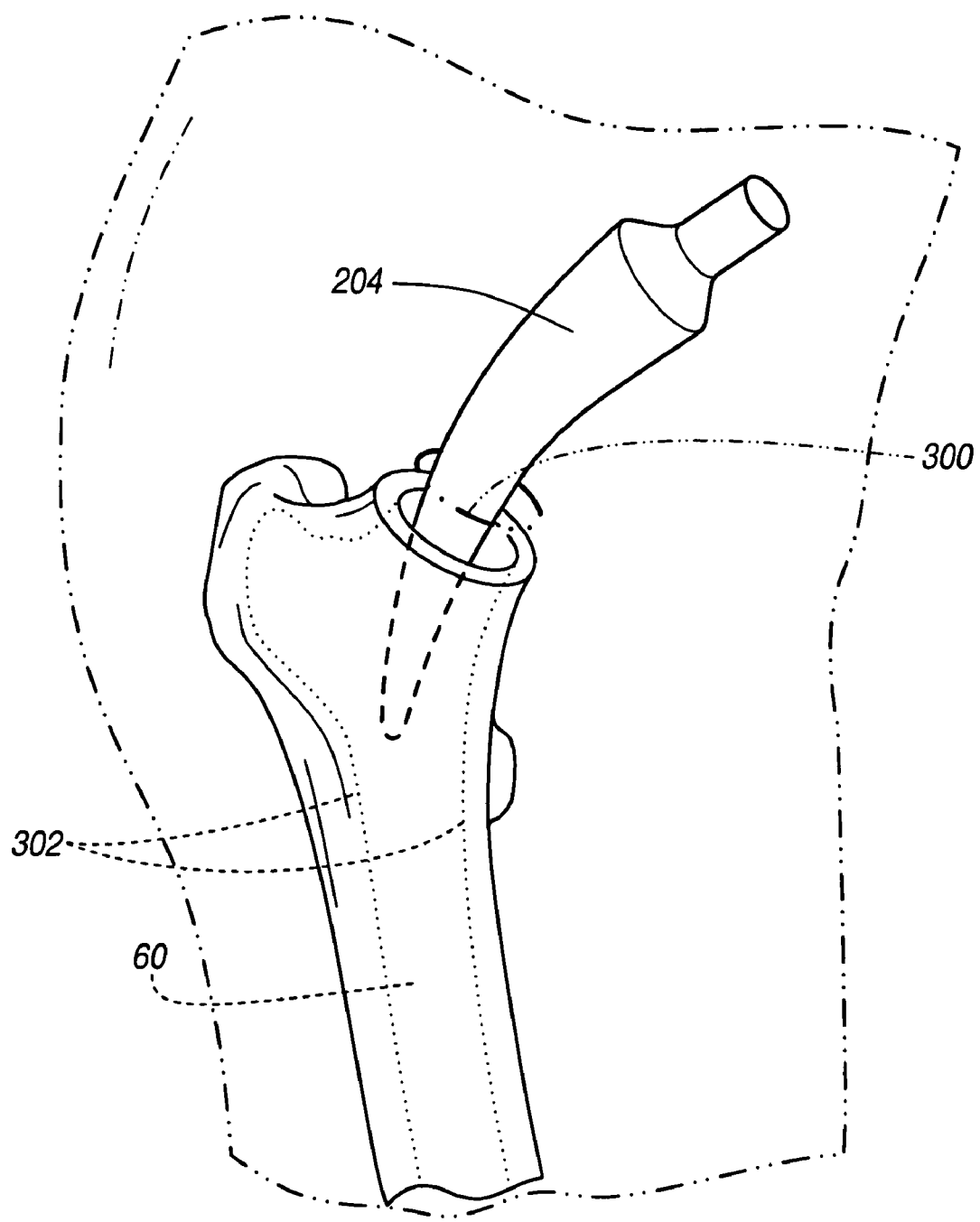
FIG. 29 is a side view of a femoral insert partially inserted through a small incision in the femur along an arcuate path according to the present teachings.

In operation, the patient is placed with the femur in the supine position. The anterior incision 300 is made through the femoral tissues, as shown in FIG. 26. The femur is rotated 90° from the anatomical position externally to point the femoral neck axis out of the anterior incision 300. Then the preparation instrument 306 is inserted through the incision 300 to form the arcuate path 302, as shown in FIG. 28. After the arcuate path 302 has been prepared, the stem member 204 is gradually inserted through incision 300 and along the arcuate path 302, as shown in FIG. 29, until the stem member 204 is fully inserted into the intramedullary canal 60, as shown in FIG. 27. The acetabulum can also be prepared for receiving the acetabular cup 312 and/or femoral head 310, by inserting preparation instruments through the incision 300, and then inserting the acetabular components into the prepared acetabulum.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

The invention claimed is:

1. A method of implanting at least a stem member of a femoral insert into an intramedullary canal of a femur, the method comprising:
   making an anterior incision for accessing the intramedullary canal, the anterior incision is located approximately over the neck region of the femur;
   providing the stem member to extend between a first end and a second end and a portion interconnecting the first end and the second end defining an arcuate profile; cutting an arcuate path through the incision into the intramedullary canal; and
   inserting the stem member of the femoral insert into the intramedullary canal through the anterior incision along an arcuate path having a substantially constant radius, the arcuate path defined by an arcuate profile of the stem member, the arcuate path extends from the anterior incision into at least a portion of the intramedullary canal, the anterior incision is made along a line that is at least approximately perpendicular to an arcuate axis of the intramedullary canal, the incision having a width that is at least approximately equal to the widest dimension of the stem member.

2. The method of claim 1, wherein the arcuate profile of the stem member is defined by a lateral portion of the stem member having a first radius and a medial portion of the stem member having a second radius.

3. The method of claim 2, further comprising:
   engaging a proximal surface of the lateral portion of the stem member with substantially only a proximal portion of a lateral surface of the intramedullary canal; and
   engaging the medial portion of the stem member with substantially only a medial surface of the intramedullary canal.

4. The method of claim 3, further comprising:
   engaging a distal surface of the lateral portion of the stem member with a distal portion of the lateral surface of the intramedullary canal.

5. The method of claim 3, wherein the first and second radii are substantially equal.

6. The method of claim 1, wherein the stem member tapers from a proximal to a distal portion in the anterior/posterior plane.

7. The method of claim 2, wherein the lateral and medial portions of the stem member converge distally.

8. The method of claim 1, wherein the arcuate profile has a constant curvature between a lateral and medial surface of the stem member.

9. The method of claim 1, wherein making an anterior incision includes making the incision substantially at 90 degrees relative to the intramedullary canal.

10. The method of claim 1, further comprising inserting femoral preparation instruments through the incision substantially along the arcuate path.

11. The method of claim 10, wherein inserting femoral preparation instruments through the incision includes inserting by image guidance.

12. The method of claim 1, further comprising cutting the arcuate path with a preparation instrument having a corresponding arcuate shape.

13. The method of claim 1, further comprising inserting a femoral head through the incision, an acetabular cup through the incision, or combinations thereof.

14. The method of claim 1, wherein inserting the stem includes moving the stem only along the arcuate path.

15. The method of claim 1, further comprising making only a single anterior incision;
wherein the anterior incision is the only incision made during a procedure for implanting the femoral insert.

16. A method of implanting at least a stem member of a femoral insert into an intramedullary canal of a patient's femur, the method comprising:
placing the patient in a supine position;
making an anterior incision adjacent to the neck of the femur;
providing the stem member with a longitudinally curved profile;
cutting an arcuate path through the incision into the intramedullary canal;
preparing the intramedullary canal to receive the stem member using a broach and without using a reamer, the broach having dimensions and an overall shape that is substantially similar to the stem member; and
inserting the stem member through the anterior incision along the arcuate path substantially matching the curved line of the stem member into the intramedullary canal.

17. The method of claim 16, wherein cutting an arcuate path further comprises cutting an arcuate path of substantially constant radius.

18. The method of claim 16, wherein making an anterior incision comprises making an anterior incision of width not exceeding any width of the stem member.

19. The method of claim 16, wherein the constant radius is defined by substantially equal radii of lateral and medial portions of the stem member.

20. The method of claim 16, further comprising inserting at least one of an acetabular cup, a femoral head, or combinations thereof through the incision.

21. The method of claim 16, further comprising preparing the acetabulum to receive an acetabular cup through the incision.

22. The method of claim 16, further comprising:
making only the anterior incision;
forming only the anterior incision relative to the intramedullary canal of the femur so that a curved path can be used to obtain access to the proximal femur and the intramedullary canal to prepare the intramedullary canal for the stem member;
wherein inserting the stem member includes moving along a path that allows an end of the stem member to define an arc.

23. The method of claim 16, further comprising making only a single anterior incision;
wherein the anterior incision is the only incision made during a procedure for implanting the femoral insert; and
wherein the anterior incision made along a line that is approximately perpendicular to an arcuate axis of the intramedullary canal.

24. The method of claim 16, wherein cutting an arcuate path includes passing the broach along the arcuate path.

25. A method of implanting a stem member and acetabular cup into a patient's femur, the method comprising:
placing the patient in a supine position;
making only a single anterior incision during said method, the single anterior incision adjacent to the neck of the femur;
cutting an arcuate path through the anterior incision into at least a portion of the intramedullary canal of the femur, the anterior incision made along a line that is approximately perpendicular to an arcuate axis of the intramedullary canal;
providing a stem member having a portion defined by the arcuate path;
inserting the stem member through the anterior incision along the arcuate path into the intramedullary canal;
reaming the acetabulum superiorly through the anterior incision; and
inserting an acetabular cup superiorly through the anterior incision.

26. The method of claim 25, further including inserting a femoral head inferiorly through the incision.

27. The method of claim 25, further comprising making only a single anterior incision;
wherein the anterior incision is the only incision made during a procedure for implanting the stem member.

28. A method of implanting a femoral insert into an intramedullary canal of a femur, comprising:
making an anterior incision for accessing the intramedullary canal;
cutting an arcuate path through the incision into the intramedullary canal;
resecting the femur head;
removing a sufficient amount of bone tissue adjacent to the femoral neck and intramedullary canal such that at least a portion of the femoral insert is capable of being received into the intramedullary canal; and
only removing bone from the direction where the femoral head is removed and not by placing a reamer axially down the intramedullary canal;
placing at least a portion of the femoral insert into the intramedullary canal;
wherein the femoral insert comprises a member having a lateral surface and a spaced and opposed medial surface;
wherein the lateral surface of the member has a first radius and the medial surface of the member has a second radius;
wherein the lateral surface is adapted to engage at least a portion of a lateral surface of the intramedullary canal and the medial surface is adapted to engage at least a portion, of a medial surface of the intramedullary canal; and
wherein the first radius of the lateral surface of the member is substantially equal to the second radius of the medial surface of the member.

29. The method of claim 28, further comprising making only a single anterior incision;
wherein the anterior incision is the only incision made during a procedure for implanting the femoral insert.

* * * * *

UNITED STATES PATENT AND TRADEMARK OFFICE
CERTIFICATE OF CORRECTION

PATENT NO. : 7,494,509 B1
APPLICATION NO. : 10/892460
DATED : February 24, 2009
INVENTOR(S) : Troy W. Hershberger et al.

It is certified that error appears in the above-identified patent and that said Letters Patent is hereby corrected as shown below:

Title Page; item (56);

Page 1, right column, References cited, U.S. Pat. Document No. 4,792,339; *"Tepic"* *should be --Tepi--*

Page 2, left column, References cited, Other Document, Article Entitled "Less, pain, quicker recovery, shorter hospital stay for hip-replacement surgery"; *"hopsital" should be --hospital--*

Page 3, left column, References cited, Other Documents, Kegging Two Incision Approach as performed by Kristaps J. Keggi, M.D., printout of Power Point Presentation presented at Yale Orthopaedic Alumni [insert meeting] in Banff; *insert --meeting-- before "in Banff"*

Page 3, left column, References cited, Other Documents, Light, M.D., et al., Anterior [insert Approach] to Hip Arthroplasty, Clinical Orthopaedics and Related Research CJB Lippincott, Co; *insert --Approach-- before "to Hip Arthroplasty"*

UNITED STATES PATENT AND TRADEMARK OFFICE
CERTIFICATE OF CORRECTION

PATENT NO. : 7,494,509 B1
APPLICATION NO. : 10/892460
DATED : February 24, 2009
INVENTOR(S) : Troy W. Hershberger et al.

It is certified that error appears in the above-identified patent and that said Letters Patent is hereby corrected as shown below:

In column 1, line 44; *"removes" should be --remove--*

In column 4, line 66; *"a" should be --an--*

In column 7, line 22; *delete "lateral"*

In column 7, line 43; *delete "of the medial surface"*

In column 12, line 55; *delete ","*

Signed and Sealed this

Second Day of June, 2009

JOHN DOLL
*Acting Director of the United States Patent and Trademark Office*